US010267792B2

(12) United States Patent
Buvid et al.

(10) Patent No.: US 10,267,792 B2
(45) Date of Patent: Apr. 23, 2019

(54) DEVICE FOR DETECTING TOXIC SHOCK SYNDROME TOXINS AND METHOD OF MAKING THE SAME

(71) Applicant: International Business Machines Corporation, Armonk, NY (US)

(72) Inventors: Daniel J. Buvid, Rochester, MN (US); Eric J. Campbell, Rochester, MN (US); Sarah K. Czaplewski, Rochester, MN (US); Christopher W. Steffen, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 204 days.

(21) Appl. No.: 15/261,522

(22) Filed: Sep. 9, 2016

(65) Prior Publication Data

US 2018/0074050 A1  Mar. 15, 2018

(51) Int. Cl.
*G01N 21/75* (2006.01)
*G01N 33/543* (2006.01)
*G01N 33/558* (2006.01)

(52) U.S. Cl.
CPC ..... *G01N 33/54386* (2013.01); *G01N 33/558* (2013.01); *G01N 2333/31* (2013.01)

(58) Field of Classification Search
CPC ........... G01N 33/54386; G01N 33/558; G01N 2333/31
See application file for complete search history.

(56) References Cited

U.S. PATENT DOCUMENTS

| 5,437,978 A | 8/1995 | Ubukata et al. |
| 5,685,872 A | 11/1997 | Syverson |
| 8,546,093 B2 | 10/2013 | Song et al. |
| 9,227,996 B2 | 1/2016 | Blackwell et al. |

(Continued)

FOREIGN PATENT DOCUMENTS

| CN | 102135540 A | 7/2011 |
| CN | 102323416 A | 1/2012 |

OTHER PUBLICATIONS

Marshall, et al., "Effect of Lipid and Fatty Acid Composition of Phospholipid Vesicles on Long-Term Stability and Their Response to *Staphylococcus aureus* and *Pseudomonas aeruginosa* Supernatants", Langmuir, American Chemical Society, May 13, 2013, 2 pp.

(Continued)

*Primary Examiner* — Dennis White
(74) *Attorney, Agent, or Firm* — Patterson + Sheridan, LLP

(57) ABSTRACT

A device for detecting toxic shock syndrome toxins includes a pad and a membrane coupled to the pad. The pad includes first antibodies that include a first particular antibody and a second particular antibody. Each of the first antibodies are associated with toxic shock syndrome toxin one (TSST-1). The first particular antibody is configured to react with a TSST-1 antigen to form an antibody complex. The membrane includes a first zone that includes an immobilized second antibody configured to react with the antibody complex to cause a first indication. The membrane further includes a second zone that includes a third antibody configured to react with the second particular antibody to cause a second indication.

17 Claims, 8 Drawing Sheets

(56) References Cited

U.S. PATENT DOCUMENTS

2003/0073073 A1\* 4/2003 Wolde-Mariam .... G01N 33/558
                                                   435/5
2004/0249122 A1   12/2004 Blazyk
2006/0134796 A1\* 6/2006 Bommarito ............. C12Q 1/04
                                                   436/166
2013/0143953 A1   6/2013 Kumar-Singh et al.

OTHER PUBLICATIONS

"Revolutionary Burns Dressing Could Save Young Lives", University of Bath, Mar. 25, 2013, viewed Feb. 23, 2016 http://www.bath.ac.uk/news/2013/03/25/burns-dressing-prototypei, 4 pp.

Wells, et al., Production and Characterization of Monoclonal Antibodies to Toxic Shock Syndrome Toxin 1 and Use of a Monoclonal Antibody in a Rapid, One-Step Enzyme-Linked Immunosorbent Assay for Detection of Picogram Quantities of Toxic Shock Syndrome Toxin 1, Journal of Clinical Microbiology, Mar. 1987, pp. 516-521.

Veeh, et al., "Detection of *Staphylococcus aureus* Biofilm on Tampons and Menses Components", The Journal of Infectious Diseases, Sep. 2003, pp. 519-530.

\* cited by examiner

```
                                                                    800
                                                                 ↙

┌─────────────────────────────────────────────────────────┐
  │ Deposit a second antibody on a first zone of a membrane, where the │   802
  │ second antibody is reactive with an antibody complex to produce a first │
  │ indication, and where the antibody complex includes a first antibody │
  │            coupled to a TSST-1 antigen                  │
  └─────────────────────────────────────────────────────────┘
                              │
                              ▼
  ┌─────────────────────────────────────────────────────────┐
  │ Deposit a third antibody on a second zone of the membrane, where the │   804
  │ third antibody is reactive with a fourth antibody to produce a second │
  │                        indication                      │
  └─────────────────────────────────────────────────────────┘
```

DEVICE FOR DETECTING TOXIC SHOCK SYNDROME TOXINS AND METHOD OF MAKING THE SAME

I. FIELD OF THE DISCLOSURE

The present disclosure relates generally to detection of toxic shock syndrome toxins.

II. BACKGROUND

Toxic shock syndrome (TSS) is a life-threatening complication of a bacterial infection, the can result from a variety of situations, such as skin infections, burns, nosebleeds, post-childbirth, and post-surgery. For example, TSS may result from a body's immune reaction to toxins produced by *staphylococcus aureus* (Staph) bacteria. Initial symptoms of TSS may be similar to symptoms of influenza ("the flu"). In some instances, TSS can progress quickly and can be fatal within days if left untreated. Possible complications with TSS include liver failure, kidney failure, heart failure, shock, and gangrene.

Absorbent articles, such as dressings and absorbent pads, may create an environment in which Staph bacteria can multiply and produce toxins that cause TSS. Conventional tests for TSS include a series of blood tests which can take hours or days before test results are available. While waiting for the test results, TSS may progress and cause irreversible damage.

III. SUMMARY OF THE DISCLOSURE

According to an embodiment, a device for detecting toxic shock syndrome toxins includes a pad and a membrane coupled to the pad. The pad includes first antibodies that include a first particular antibody and a second particular antibody. Each of the first antibodies are associated with toxic shock syndrome toxin one (TSST-1). The first particular antibody is configured to react with a TSST-1 antigen to form an antibody complex. The membrane includes a first zone that includes an immobilized second antibody configured to react with the antibody complex to cause a first indication. The membrane further includes a second zone that includes a third antibody configured to react with the second particular antibody to cause a second indication. The first indication, the second indication, or both, may indicate a positive test result or a negative test result of TSST-1 antigens. Because the device detects TSS toxins, the device may be more accurate at detecting TSS than devices that only detect Staph bacteria which produce TSS toxins.

According to another embodiment, a device for detecting toxic shock syndrome toxins includes a pad and a membrane coupled to the pad. A reaction zone of the pad includes first antibodies that include a first particular antibody coupled to a first enzyme and includes a second particular antibody coupled to a second enzyme. Each of the first antibodies are associated with toxic shock syndrome toxin one (TSST-1). The first particular antibody is configured to react with a TSST-1 antigen to form an antibody complex. A test zone of the membrane includes a first dye substrate and an immobilized second antibody. The immobilized second antibody is configured to react with the antibody complex to enable the first enzyme to cause the first dye substrate to release a first dye. A control zone of the membrane includes a second dye substrate and a third antibody. The third antibody is configured to react with the second antibody to enable the second enzyme to cause the second dye substrate to release a second dye.

According to another embodiment, a method of producing (e.g., making) a membrane for detecting toxic shock syndrome toxins includes depositing a second antibody on a first zone of the membrane. The second antibody is reactive with an antibody complex to cause a first indication. The antibody complex includes a first antibody coupled to a TSST-1 antigen. The method also includes depositing a third antibody on a second zone of the membrane. The third antibody is reactive with a fourth antibody to cause a second indication.

IV. BRIEF DESCRIPTION OF THE DRAWINGS

FIG. 8 is a flow diagram showing an example of a method of manufacturing a membrane for detecting toxic shock syndrome toxins.

V. DETAILED DESCRIPTION

The present disclosure relates to a device for detecting toxic shock syndrome (TSS) and to a method of making the device. The device may be configured to detect TSS toxins, such as TSS toxin one (TSST-1). For example, the device may indicate a presence of TSS toxins (e.g., TSST-1 antigens) in a fluid, such as a bodily fluid.

The device includes a pad (e.g., a reaction zone) and a membrane (e.g., a test zone, a control zone, or both). The pad and the membrane may include one or more reagents (e.g., antibodies) that react with TSST-1 antigens and that react with other reagents. The device may receive or absorb a fluid that includes the TSST-1 antigens. To illustrate, the TSST-1 antigens in the fluid may bind (e.g., react) with first antibodies included in the pad to form antibody complexes. The antibody complexes may react with second antibodies included in the membrane to cause an indication. For example, the antibody complexes may be transported to the membrane by the fluid, and the antibody complexes may bind with the second antibodies to produce or generate a color change (e.g., release a dye) in the membrane to indicate a positive test result of the presence of TSST-1 antigens.

The device may include or correspond to a test strip, a testing device, a dressing, pad, or a combination thereof, as illustrative, non-limiting examples. In some implementations, one or more devices (e.g., a test strip) may be included in the wound dressing, a product and may be exposed to or receive fluid during conventional use. As compared to a conventional TSS test, such as a laboratory test, the disclosed device may be used in-situ (e.g., on site). To illustrate, the device may be portable and may provide results in-situ (e.g., on site) at or near where a fluid sample is produced without having to send the fluid sample to a laboratory (e.g., off site). The device may be used at a user's home and may be used independent of a medical professional. As compared to other tests that detect the presence of bacteria that produces TSST-1 antigens, such as Staph bacteria, the device may indicate a presence of TSS toxins, such as the TSST-1 antigens, which contribute to TSS. By detecting the TSST-1 antigens instead of the Staph bacteria, the device may be more accurate and more precise in detecting TSS as compared to a test that detects Staph bacteria without also testing for TSST-1. Additionally or alternatively, the device may more quickly produce accurate test results as compared to conventional assay methods used to test for TSST-1. For example, test results of the device may be obtained in minutes as compared to hours or days for conventional assay tests.

Figure 1:
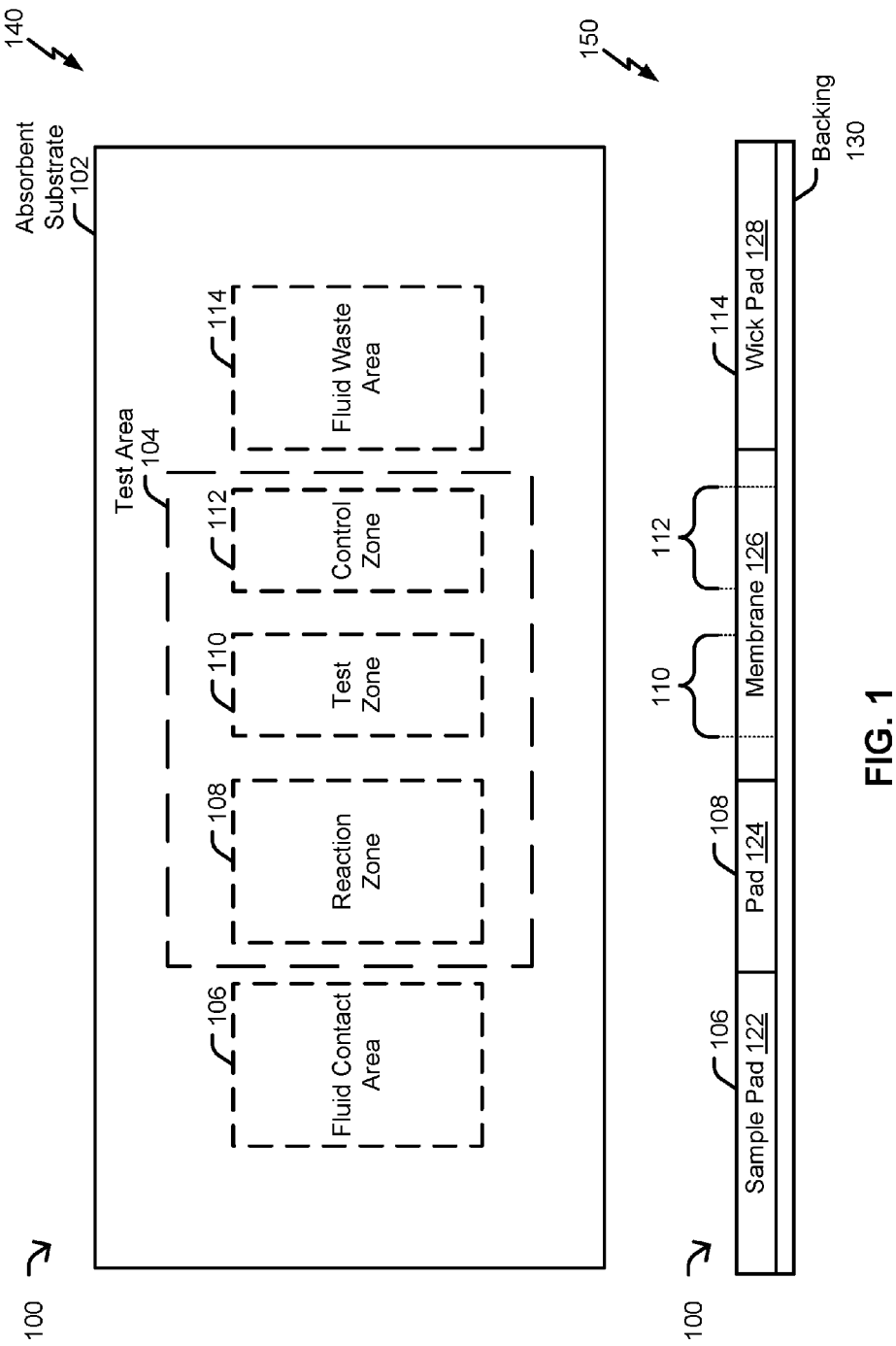
FIG. 1 is a diagram illustrating an example of a device for detecting toxic shock syndrome toxins.

Referring to FIG. 1, a top view diagram 140 and a side view diagram 150 of an example of a device 100 for detecting TSS toxins are depicted. The device 100 is configured to indicate a presence of TSS toxins. For example, the device 100 may include a plurality of reagents (e.g., proteins, antibodies, enzymes, etc.) configured to react with TSST-1 antigens and one or more additional reagents to generate the indication of a presence of TSS toxins. The indication may be a visible indication (e.g., a color change) detectable by a human or may be a reactionary indication (e.g., an amount of fluorescent or magnetic particles) detectable by an electronic reader. In some implementations, the indication may be a qualitative indication (e.g., positive or negative). Additionally or alternatively, the indication may be a quantitative indication (e.g., an amount or a concentration) of TSST-1 antigens.

Referring to the top view 140, the device 100 includes an absorbent substrate 102. Portions of the absorbent substrate 102 may be referred to as "areas" or "zones." To illustrate, the absorbent substrate 102 may include a fluid contact area 106, a reaction zone 108, a test zone 110, a control zone 112, and a fluid waste area 114. The reaction zone 108, the test zone 110, and the control zone 112, may be referred to collectively as a test area 104. These areas or zones may correspond to portions of the absorbent substrate 102 where fluid is absorbed and stored (e.g., the areas 106, 114) and where reactions take place (e.g., the test area 104).

The absorbent substrate 102 (and components thereof) may include or correspond to cellulose fibers, synthetic fibers, cellulose nanofibers, synthetic nanofibers, or a combination thereof, as illustrative, non-limiting examples. In some implementations, the fibers (or nanofibers) are arranged laterally (e.g., orientated/running in a direction from the fluid contact area 106 to the fluid waste area 114). Additionally or alternatively, the absorbent substrate 102 may include one or more hydrophilic or superhydrophilic materials. In some implementations, the absorbent substrate 102 (and components thereof) includes a plurality of narrow channels (e.g., capillary beds). The plurality of narrow channels may be laterally arranged, such as arranged in a direction from the fluid contact area 106 to the control zone 112.

The absorbent substrate 102 may be configured to transport fluid (e.g., a received bodily fluid) to the test area 104. For example, the absorbent substrate 102 may be configured to channel the fluid received outside the test area 104 to the test area 104 or a portion thereof (e.g., the reaction zone 108). The absorbent substrate 102 may be configured to transport the fluid across the test area 104 (e.g., from the reaction zone 108 to the control zone 112) and to the fluid waste area 114. To illustrate, after the fluid is received in or around the fluid contact area 106 or reaction zone 108, the fluid may migrate to the control zone 112 via the test zone 110. The fluid may travel by capillary action (e.g., wicking), by use of a hydrophilic material, by use of a hydrophobic material, or a combination thereof. The fluid may be received directly from a user or indirectly from the user. Additionally or alternatively, the fluid may be received as a result of a direct action by the user to capture the fluid or while the user is performing another task. As an illustrative, non-limiting example, a user may apply a wound dressing as a part of a treatment for a burn, and the wound dressing may receive or absorb the fluid without user intervention.

The fluid contact area 106 may include a hydrophilic material, a hydrophobic material, or a combination thereof. The fluid contact area 106 may be configured to receive a fluid sample. The fluid contact area 106 may be configured to transfer the fluid (or a portion thereof) to the reaction zone 108.

The reaction zone 108 may include first chemical compounds, such as protein complexes, that are selectively reactive with TSST-1. For example, the first chemical compounds (referred to herein as first antibodies or a first antibody) may include or correspond to antibodies for TSST-1 antigens. The first antibodies are configured to bind with the TSST-1 antigens to form antibody complexes. Each of the antibody complexes may include a first antibody bound to a TSST-1 antigen. In some implementations, the first antibody may be monovalent, polyvalent, monospecific, monoclonal, or a combination thereof. The first antibody (e.g., a conjugated antibody or a labeled antibody) of the first antibodies may be coupled or linked to an enzyme. The enzyme may include or correspond to a conjugated enzyme (e.g., a protein and one or more non-proteins). The enzyme may be configured to activate (e.g., bind with or couple with) a dye substrate and release a dye responsive to the first antibodies, the antibody complexes, or both, binding with another antibody.

The first antibodies and the antibody complexes may be free to move to other zones (e.g., the test zone 110, the control zone 112, or both) and to bind to other antibodies. To illustrate, the first antibodies and the antibody complexes may not be immobilized, bounded by, or bound to the reaction zone 108. For example, the antibody complexes (e.g., a first particular antibody of the first antibodies) may travel to the test zone 110, and the first antibodies (e.g., a second particular antibody of the first antibodies) may travel to the control zone 112 (via the test zone 110). As another example, when fluid is introduced to the reaction zone 108, the fluid may react with the first antibodies to form the antibody complexes and the fluid may pick-up (e.g., suspend), absorb, contain, or dissolve the first antibodies and the antibody complexes. The fluid may carry the first antibodies and the antibody complexes to other zones as the fluid flows within the absorbent substrate 102 (e.g., flows toward the control zone 112 or toward the fluid waste area 114). To illustrate, a first particular antibody of the first antibodies may react with a TSST-1 antigen and form an antibody complex; a second particular antibody of the first antibodies may not react with a TSST-1 antigen and may not form an antibody complex. The first particular antibody and the second particular antibody may have the same chemical structure.

The test zone 110 may be configured to release a first dye in the presence of (or upon contact with) the antibody complexes. The release of the first dye may indicate a positive test result for TSS toxins. The test zone 110 may include or correspond to a first dye substrate and may include second chemical compounds. The second chemical compounds, such as protein complexes, may be selectively reactive with the antibody complexes. For example, the second chemical compounds (referred to herein as second antibodies or a second antibody) may include or correspond to second antibodies for the antibody complex. In some implementations, the second antibodies may be monovalent, polyvalent, monospecific, monoclonal, or a combination thereof. The second antibodies may be confined to the test zone 110, may be immobilized within the test zone 110, or both. For example, the test zone 110 may include a binding agent to bind (e.g., couple) the second antibodies to or within the test zone 110. The test zone 110 and the second antibodies may be configured such that the second antibodies remain in the test zone 110, even in the presence of the fluid.

The second antibodies may be configured to bind with the antibody complexes to enable enzymes of the antibody complexes (e.g., the enzyme coupled to the first antibody) to activate the first dye substrate to release the first dye. For example, the second antibodies may be configured to bind with the TSST-1 antigen (e.g., an exposed portion of the TSST-1 antigen), which is bound to the first antibody (forming the antibody complex). The second antibodies may be configured to not bind directly with the first antibodies. The first antibodies and the second antibodies may correspond to a sandwich enzyme-linked immunoabsorbant assay (ELISA).

The control zone 112 may include or correspond to a second dye substrate and may include third chemical compounds. The first dye substrate and the second dye substrate may be different portions of a common substrate or may be different substrates. The third chemical compounds, such as protein complexes, may be reactive with the first antibodies. For example, the third chemical compounds (referred to herein as third antibodies or a third antibody) may include or correspond to antibodies that react (e.g., bind with) the first antibodies, such as anti-antibodies or conjugate antibodies of the first antibodies. The third antibodies may be configured to bind with the first antibodies to enable the enzymes to activate the second dye substrate to release the second dye. In some implementations, the third antibodies may be monovalent, polyvalent, monospecific, monoclonal, or a combination thereof.

A second dye may be released in the control zone 112 in the presence of the first antibodies. The release of the second dye may indicate a successful test (e.g., a positive test result or a negative test result) for TSS toxins, such as the first antibodies or antibody complexes have migrated from the reaction zone 108 to the control zone 112. For example, the release of the second dye may indicate that the test zone 110 is providing a correct result. The release of the second dye without a release of the first dye may indicate a negative test result for TSS toxins. A positive test result (e.g., the release of the first dye) without the release of the second dye may indicate a problem with the test, such as a false positive.

In some implementations, the third antibodies may be configured to bind with the antibody complexes, the second antibodies, or both. In other implementations, the third antibodies may be configured to not bind with the antibody complexes, the second antibodies, or both. In a particular implementation, the third antibodies may be confined to the control zone 112, may be immobilized within the control zone 112, or both. Additionally, one or more of the reaction zone 108, the test zone 110, or the control zone 112 may include other chemicals or substances (e.g., reagents) to facilitate binding reactions. For example, the pad 124, the membrane 126 or both, may include a salt and sugar mixture that may facilitate antibody binding.

In some implementations, antibodies of the zones 108-112 may be arranged or concentrated in a pattern, such as arranged or concentrated to form one or more lines or shapes within a particular zone. For example, the second antibodies may be bound to the test zone 110 in a pattern of shapes or intersecting lines (e.g., a plus symbol, an "x" symbol, a minus symbol, etc.), so that when the second antibodies react with the antibody complexes the indication (e.g., a color change) has the same shape as the pattern.

The fluid waste area 114 may be configured to transport (e.g., wick) the fluid away from the test area 104. The fluid waste area 114 may be configured to absorb and store excess fluid. For example, the fluid waste area 114 may include hydrophilic materials, multiple layers of materials, or both to absorb and store the fluid.

Although the areas 106, 114 and the zones 108-112 are illustrated in FIG. 1 as having similar sizes and shapes, in other implementations one or more of the areas 106, 114, the zones 108-112, or a combination thereof, may have a different size or shape from the areas 106, 114 and the zones 108-112. For example, one or more zones of the zones 108-112 may be shaped like a line (e.g., a high aspect ratio rectangle). To illustrate, the test zone 110, the control zone 112, or both, may be shaped as a rectangle with a high aspect ratio.

Referring to the side view 150, the absorbent substrate 102 may include a sample pad 122, a pad 124, a membrane 126, a wick pad 128, and a backing 130. The areas 106, 114 or the zones 108-112 of the top view 140 may be included in or may correspond to components of the absorbent substrate 102, such as the sample pad 122, the pad 124, the membrane 126, and the wick pad 128. For example, the sample pad 122 may include or correspond to the fluid contact area 106. To illustrate, the fluid contact area 106 may represent a portion of the sample pad 122 where fluid (e.g., a bodily fluid) is received or absorbed from a user. The sample pad 122 may be configured to receive the fluid and transfer the fluid to the pad 124. For example, the fluid may travel by capillary action (e.g., wicking), by use of a hydrophilic material, by use of a hydrophobic material, or a combination thereof. In some implementations, the sample pad 122 may include or correspond to a filter pad configured to filter (e.g., remove or capture) debris or solid particles from the fluid.

The pad 124 may be coupled to and located between the sample pad 122 and the membrane 126. The pad 124 may include or correspond to the reaction zone 108. For example, the reaction zone 108 may represent a portion of the pad 124 where one or more reactions occur (e.g., where reagents react with TSST antigens). The pad 124 may include glass fibers, polyester fibers, synthetic fibers, or a combination thereof, as illustrative, non-limiting examples. Additionally or alternatively, the pad 124 may include nanofibers. Fibers of the pad 124 may be configured to form a plurality of narrow channels that enable the fluid to flow from the sample pad 122 to the membrane 126. For example, the plurality of narrow channels may provide a path for the fluid to flow by capillary action. In some implementations, the pad 124 may be a conjugate pad (e.g., include a conjugated antibody). In other implementations, the pad 124 may include or correspond to a release pad, a labelled pad, a ligand pad, or a combination thereof.

The membrane 126 may be coupled to and located between the pad 124 and the wick pad 128. The membrane 126 may include or correspond to the test zone 110, the control zone 112, or both. The test zone 110, the control zone 112, or both, may be included in the membrane 126. For example, the test zone 110 may correspond to a first portion of the membrane 126 and the control zone 112 may correspond to a second portion of the membrane 126. In some implementations, the membrane 126 may include or correspond to a membrane pad, a cellulose membrane, a nitrocellulose membrane, a lateral flow membrane, or a combination thereof.

The membrane 126 may include a plurality of narrow channels or pores that enable the fluid to flow from the membrane 126 to the wick pad 128. For example, the plurality of narrow channels or pores may provide a path for the fluid to flow by capillary action. The membrane 126 may be configured to receive the reagents from the pad 124 and to support reactions between the second antibodies and the antibody complexes. The membrane 126 may also be configured to support reactions between the third antibodies and the antibody complexes, the first antibodies, or both. The membrane 126 may be further configured to transfer the reagents (e.g., the fluid, the TSST-1 antigens, the unreacted first antibodies, the antibody complexes, or a combination thereof) to the wick pad 128 via the test zone 110 and the control zone 112.

The wick pad 128 may be coupled to the membrane 126. The wick pad 128 may include or correspond to an absorbent pad, a sink pad, a fluid reservoir, or a combination thereof, as illustrative, non-limiting examples. The wick pad 128 may include or correspond to the fluid waste area 114. For example, the fluid waste area 114 may represent a portion of the wick pad 128 where the fluid (e.g., excess fluid) is stored after the fluid has moved across the absorbent substrate 102. A combination of one or more of the sample pad 122, the absorbent substrate 102, or the wick pad 128, may exert force upon the fluid to move the fluid laterally across the test area 104.

One or more of the sample pad 122, the pad 124, the membrane 126, or the wick pad 128 may partially overlap adjacent pads or membranes. For example, the sample pad 122 may partially overlap the pad 124. Additionally or alternatively, the pad 124 and the wick pad 128 may partially overlap the membrane 126.

In some implementations, the device 100 may include the backing 130. The backing 130 may be coupled to the absorbent substrate 102. The backing 130 may be formed from plastic, a hydrophobic material, or both, as illustrative, non-limiting examples. In a particular implementation, the backing 130 may include an adhesive or may correspond to an adhesive backing. For example, the backing 130 may include a bandage adhesive in implementations in which the device 100 is a wound dressing. In other implementations, the device 100 may not include the backing 130.

During operation of the device 100 to detect a presence of TSS toxins, the device 100 may receive a fluid. For example, a bodily fluid is received at the fluid contact area 106. The fluid includes TSST-1 antigens and flows to the reaction zone 108 where the TSST-1 antigens react with the first antibodies (e.g., the first particular antibody) of the reaction zone 108 to form antibody complexes. The antibody complexes are transported by the fluid to the test zone 110 where the antibody complexes react with the second antibodies to produce an indication. For example, enzymes coupled to the first antibodies of the antibody complexes react with the first dye substrate of the test zone 110 to release the first dye. The release of the first dye in the test zone 110 indicates a positive test for TSS toxins. Additionally, the first antibodies (e.g., the second particular antibody) or the antibody complexes (including the first particular antibody coupled to the TSST-1 antigen) may be transported to the control zone 112 where the first antibodies, the antibody complexes, or both react with the third antibodies to produce a second indication. For example, the enzymes of the first antibodies, the antibody complexes, or both, react with the second dye substrate of the test zone 110 to release the second dye. A more detailed explanation of operations of the device 100 is described with reference to FIGS. 2-6.

The device 100 may be utilized by a user in-situ (e.g., on site). For example, the user may administer a test at the user's convenience, such as without a visit to a medical professional, a medical establishment, or a laboratory. Administration of the test and the use of the device 100 may vary depending on a particular implementation of the device 100. For example, in implementations in which the device 100 corresponds to a testing strip, a user may place the testing strip in contact with a bodily fluid of the user. For example, the testing strip may be placed in contact with exudate from a surgical incision or a burn or placed in contact with urine. The testing strip may receive the fluid. After receiving the fluid, the fluid may migrate from the reaction zone 108 to the control zone 112 and the testing strip may output an indication of a result of the test, such a positive test result or a negative test result.

The article may output an indication of a result of the test shortly after conventional use. The article may retain the indication for observation by the user at a later time.

In an implementation in which the device 100 corresponds to an electronic testing device, the user may activate the electronic testing device and apply the absorbent substrate 102 to a bodily fluid of the user. For example, the user may swab an affected area or may urinate on the testing device. Alternatively, the test may be activated by using a button or other selector to cause the device 100 to take in a sample of the bodily fluid. The electronic testing device may output an indication of a result of the test, such a positive test result, a negative test result, an inconclusive test result, a concentration off TSS toxins, or a combination thereof.

In an implementation in which the device 100 corresponds to a wound dressing, the user or a medical professional may apply (e.g., affix with adhesive or wrap) the wound dressing to a wound, a burn, a surgical incision, or a combination thereof. After the wound dressing is applied, the absorbent substrate of the wound dressing may contact or receive a bodily fluid. After the bodily fluid (e.g., wound exudate) is transported from the reaction zone 108 to the test zone 110, the wound dressing may output an indication of a result of the test, such as a positive test result or a negative test result. The result may be retained for observation by the user when the user changes or discards the wound dressing.

In some implementations, colored particles, fluorescent particles, or magnetic particles may be used in place of the enzymes coupled to the first antibodies. For example, a colored particle may be coupled to or linked to each of the first antibodies (e.g., conjugated antibodies). As an illustrative, non-limiting example, the colored particles may include colored latex or gold (e.g., colloidal gold). In some implementations, the colored particles may include or correspond to nanometer sized particles. In implementations in which gold particles are used, the gold particles may become concentrated in the test zone 110, the control zone 112, or both, responsive to the first antibodies or the antibody complexes bind with the second antibodies, the third antibodies, or both. The concentrated gold particles may reflect light (e.g., produce or generate a color indication) responsive to reaching or exceeding a threshold concentration (e.g., a sensitivity associated with the device 100). The gold particles may not reflect light (e.g., reflect light below a visible threshold) before reacting with the second antibodies, the third antibodies, or both or until a concentration of the gold particles exceeds the threshold concentration. Alternatively, a fluorescent particle or a magnetic particle may be coupled to (e.g., linked to) each of the first antibodies. In such implementations, an electronic reader may be used to detect an amount of fluorescent particles or an amount magnetic particles and to output a quantitative (e.g., numerical) result, as described with reference to FIG. 5. If fluorescent particles or magnetic particles are used in place of enzymes, the device 100 may include or correspond to a fluorescent immunoassay (FIA) or a magnetic immunoassay (MIA), respectively.

In other implementations, the test area 104 may include multiple test zones, multiple control zones, or a combination thereof. Although the control zone 112 is illustrated in FIG. 1 as included in the test area 104, in other implementations the control zone 112 may be omitted from the test area 104 (e.g., may be external to the test area 104) or may be omitted from the device 100.

Although the reaction zone 108 is illustrated as being separate from the control zone 112 in FIG. 1, in other implementations the reaction zone 108 may be adjacent to the control zone 112. In a particular implantation, the reaction zone 108 may be adjacent to both the test zone 110 and the control zone 112. For example, the reaction zone 108, the test zone 110, and the control zone 112 may form a "Y" shape, with the test zone 110 and the control zone 112 representing the branches of the "Y."

The device 100 may include or correspond to a test strip, a testing device, a wound dressing (e.g., a bandage), a hygiene product, or an applicator, as illustrative, non-limiting examples. In some implementations, the device is a test strip and may be included in a product. In a particular implementation, the product may include multiple test strips.

The device 100 may include or correspond to a lateral flow test, a sandwich enzyme-linked immunoabsorbant assay (ELISA), a competitive ELISA, or a combination thereof, as illustrative, non-limiting examples. For example, in a particular implementation the device 100 is a test strip, and the test strip may be a lateral flow type test. "Lateral" as used herein designates that fluid moves across the device 100 and does not designate an orientation of the device 100. As another example, in another particular implementation, the device 100 is a wound dressing, and the wound dressing may include one or more sandwich ELISAs. In other implementations, the device 100 may include or correspond to a direct ELISA or an indirect ELISA. For example, when the device 100 corresponds to a test strip, the device 100 may correspond to a direct ELISA. As another example, when the device 100 corresponds to a wound dressing, the device 100 may include one or more direct ELISAs.

Thus, FIG. 1 illustrates an example of a device 100 for detecting TSS toxins. By detecting TSS toxins, such as TSST-1, the device 100 may indicate a presence of the TSS toxins as opposed to indicating a presence of Staph bacteria which may or may not produce the TSS toxins. Thus, the device 100 may reduce false positive test results for TSS toxins and may be more accurate than tests that detect the presence of Staph bacteria. Additionally, the device 100 allows for in-situ testing (e.g., at home or without a medical professional) as opposed to conventional laboratory assays. Thus, the device 100 may provide faster and more convenient detection of TSS as compared to conventional laboratory assays.

Figure 2:
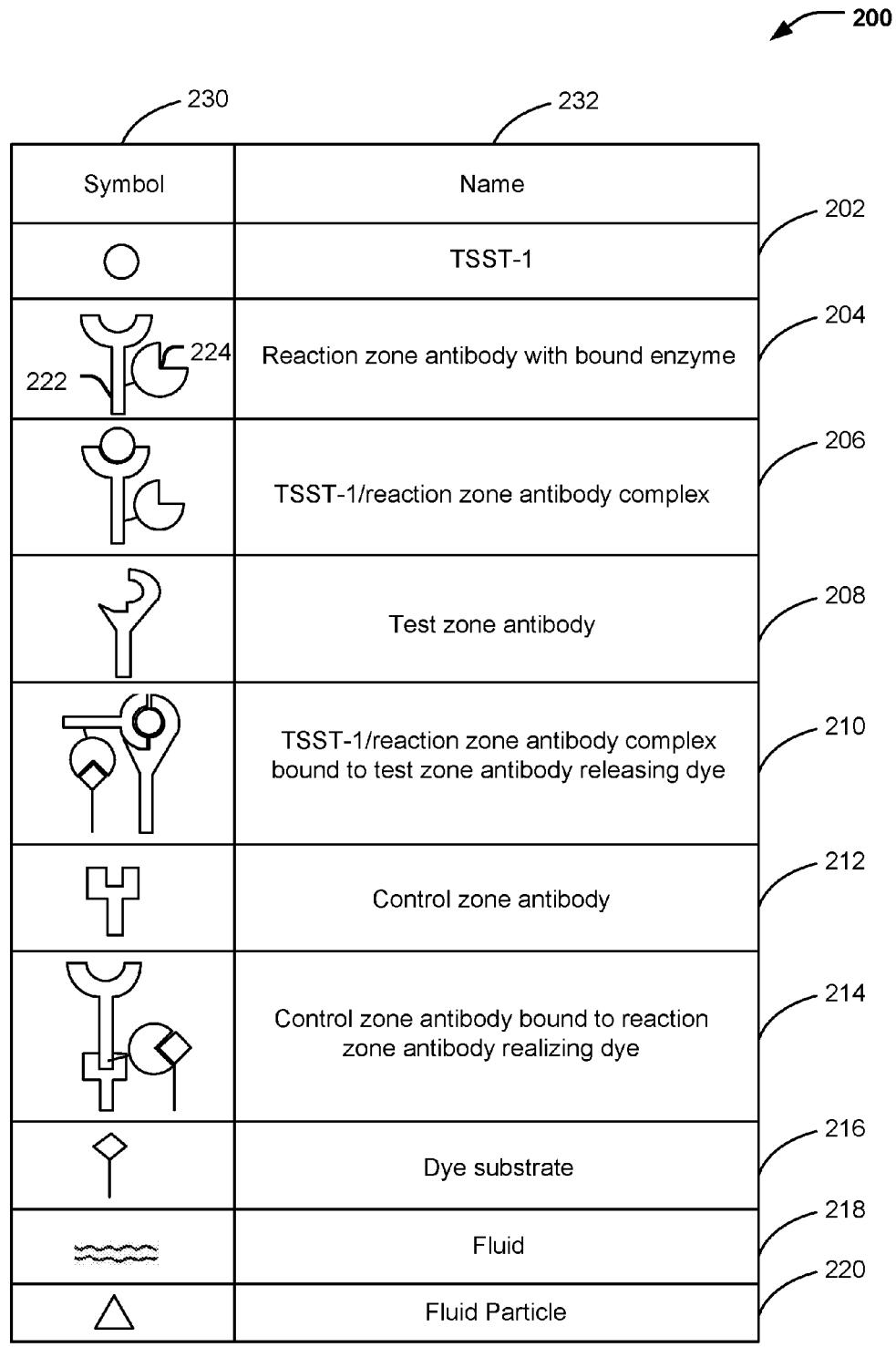
FIG. 2 is a diagram illustrating reactions associated with a device for detecting toxic shock syndrome toxins.
Figure 3:
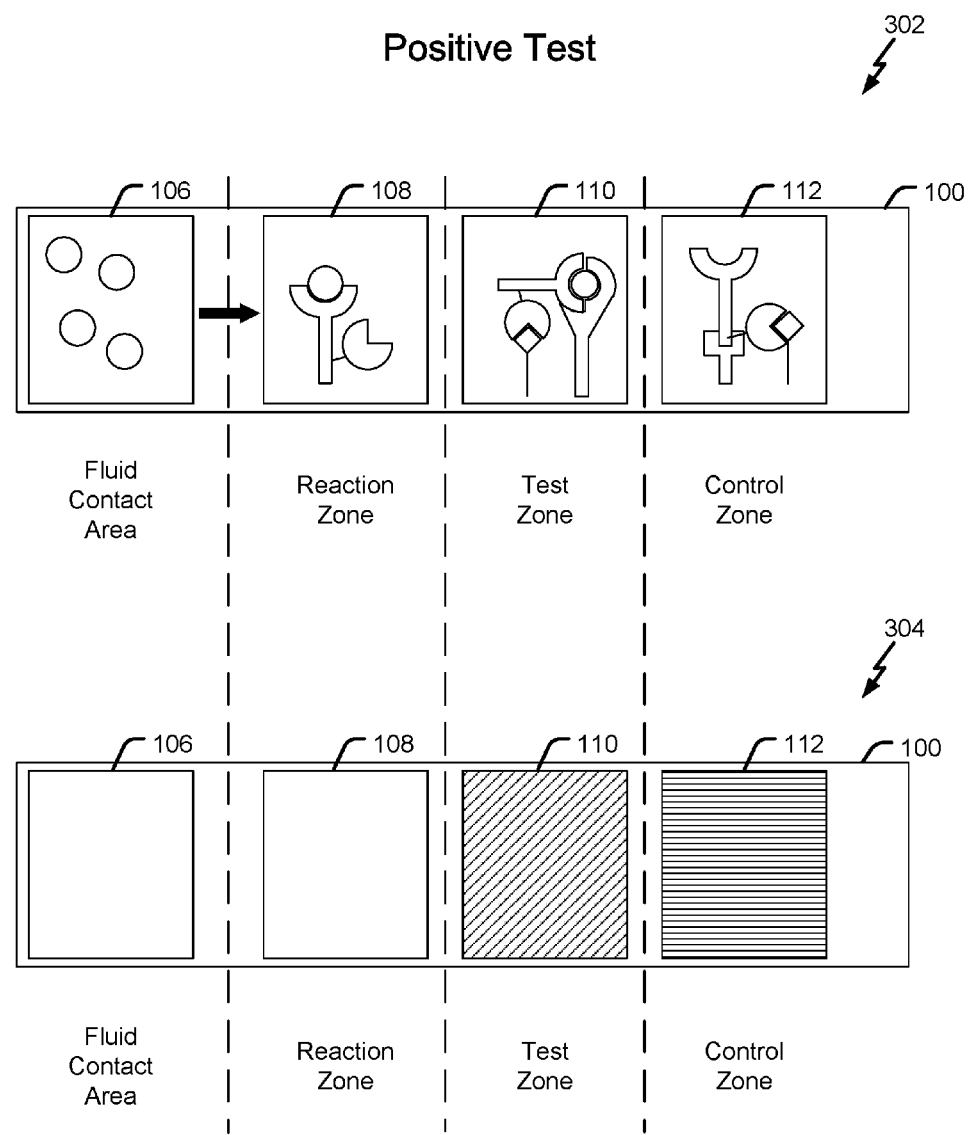
FIG. 3 is a diagram illustrating a positive test result of a device for detecting toxic shock syndrome toxins.
Figure 4:
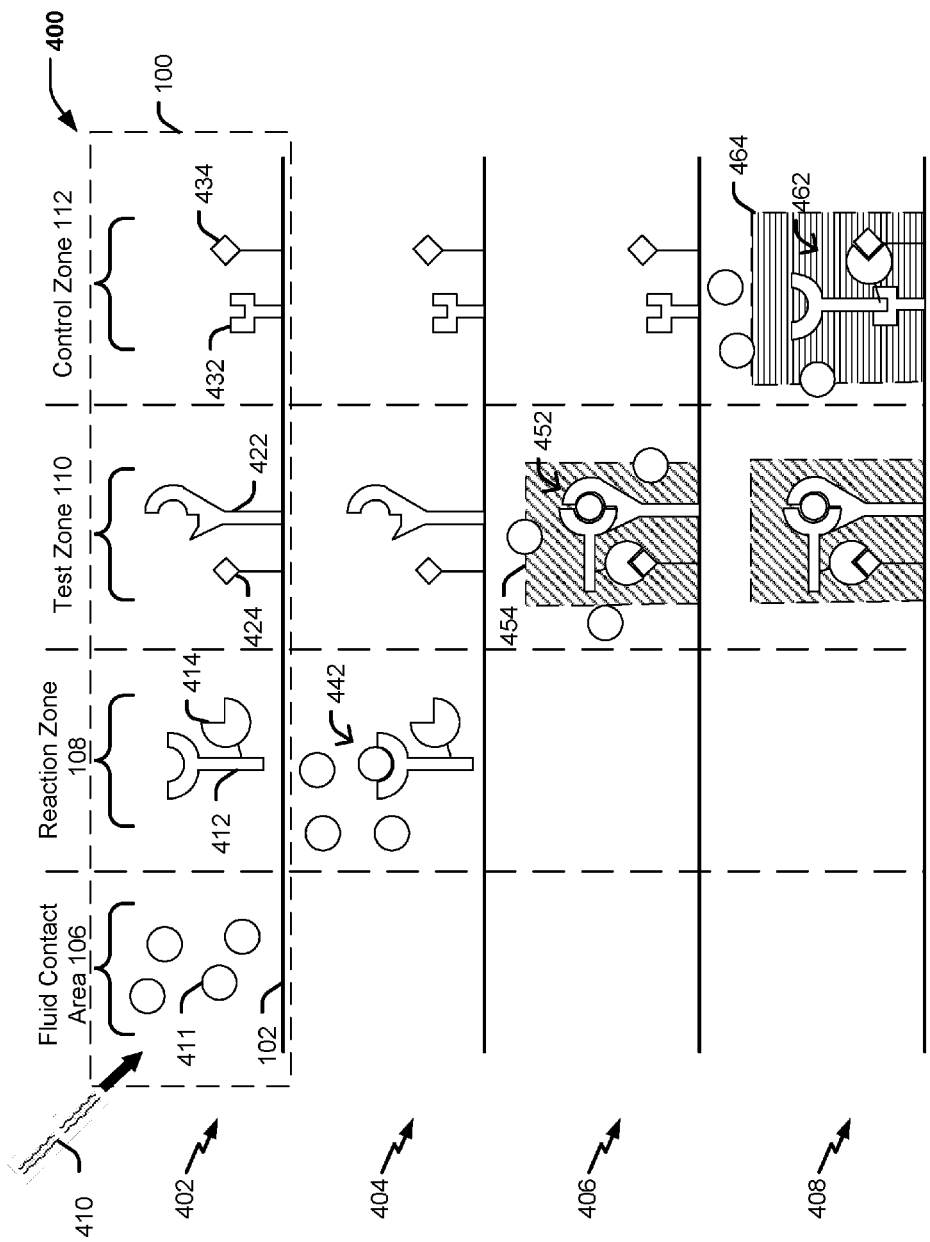
FIG. 4 is a diagram illustrating example reactions associated with a positive test result of a device for detecting toxic shock syndrome toxins.
Figure 5:
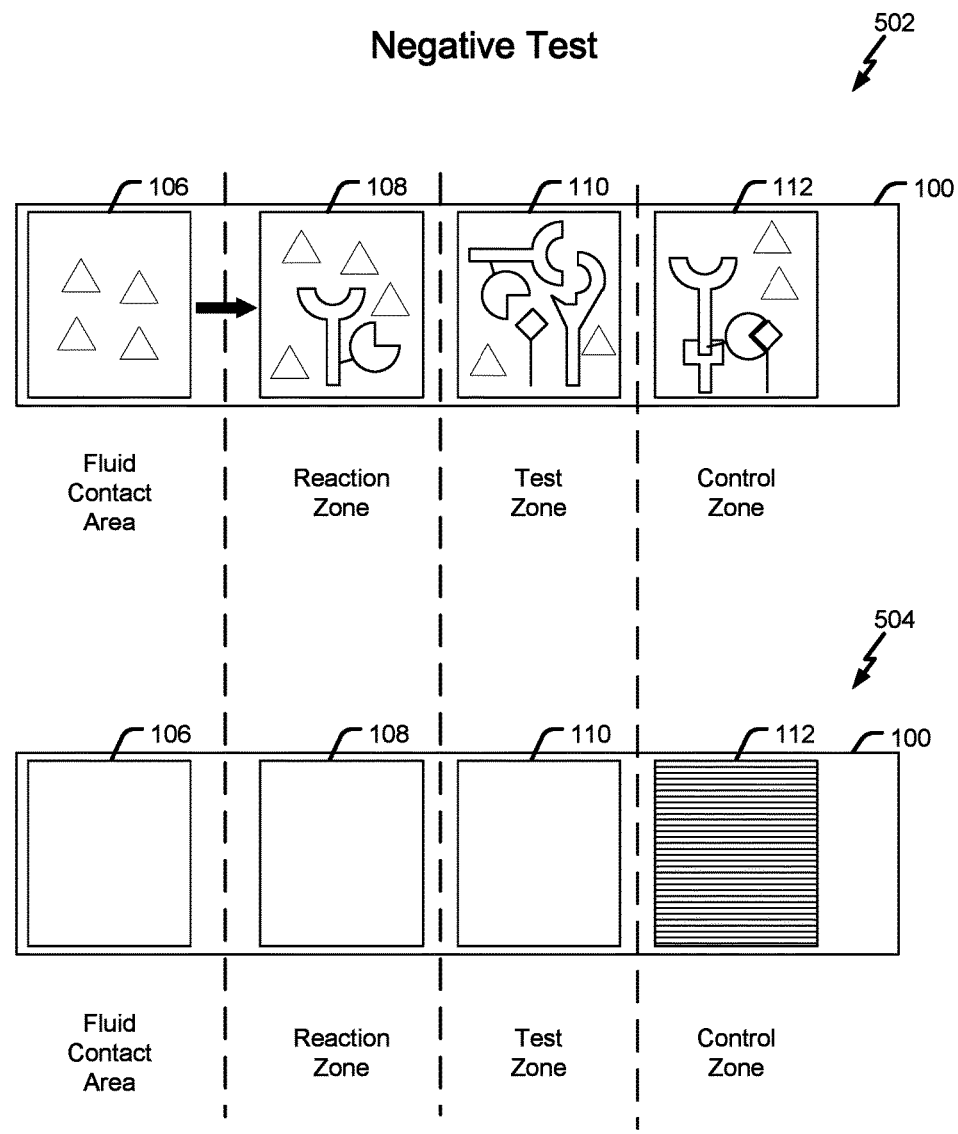
FIG. 5 is a diagram illustrating a negative test result of a device for detecting toxic shock syndrome toxins.
Figure 6:
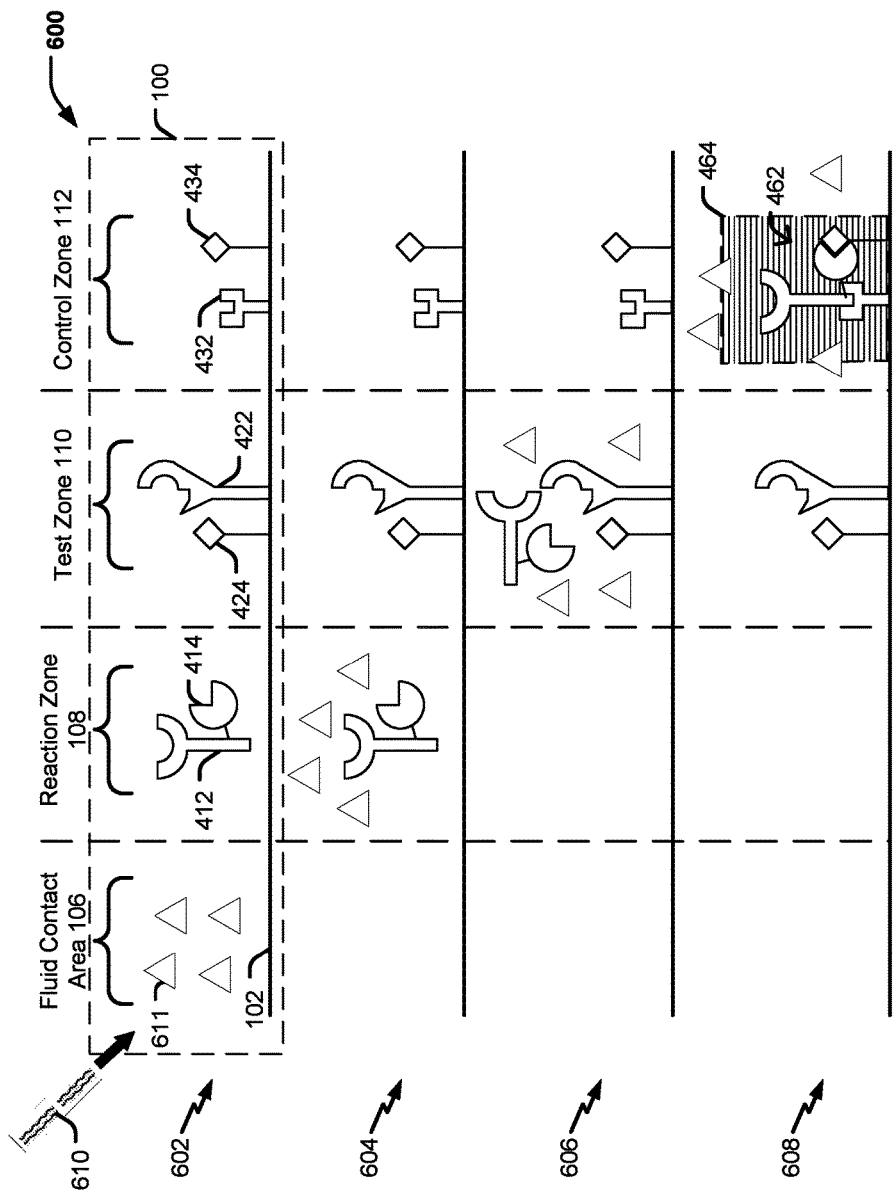
FIG. 6 is a diagram illustrating example reactions associated with a negative test result of a device for detecting toxic shock syndrome toxins.

Referring to FIG. 2, a diagram 200 illustrates symbolic examples of reagents and antibody reactions (e.g. bindings) for detecting toxic shock syndrome toxins. FIG. 2 may be used as a legend for diagrams of FIGS. 3-6. FIGS. 3 and 4 depict example illustrations of a positive test result and FIGS. 5 and 6 depict example illustrations of a negative test result. The reagents (e.g., antibodies) of FIG. 2 may include or correspond to the reagents described with respect to FIG. 1. FIG. 2 illustrates the various reactions and bindings of a device, such as the device 100 of FIG. 1 for detecting toxic shock syndrome toxins. One or more of the antibody reactions may occur at the device 100 of FIG. 1.

Diagram 200 depicts a table that includes a symbol column 230 and a name column 232 and includes rows of reagents. Row 202 illustrates a TSST-1 antigen as a circle. Row 204 illustrates a first antibody 222 of a reaction zone (e.g., the reaction zone 108 of FIG. 1) coupled to an enzyme 224. Row 206 illustrates the first antibody of the reaction zone binding with the TSST-1 antigen to form an antibody complex. Row 208 illustrates a second antibody of a test zone, such as the test zone 110 of FIG. 1. Row 210 illustrates the antibody complex binding with the second antibody in the test zone. In a particular implementation, the binding of the antibody complex with the second antibody may release a dye. The second antibody may not bind with the first antibody.

Row 212 illustrates third antibodies of a control zone, such as the control zone 112 of FIG. 1, coupled to a second enzyme. Row 214 illustrates the first antibody of the reaction zone, such as the reaction zone 108 of FIG. 1, binding with the third antibody in the control zone to release a dye. The third antibody may not bind with the second antibody, the antibody complex, or both. Row 216 illustrates a dye substrate, such as the first dye substrate of the reaction zone 108 of FIG. 1 or the second dye substrate of the control zone 112 of FIG. 1. The dye substrate may react with an enzyme, such as the enzyme 224 coupled to the first antibody 222, to release a dye. Row 218 illustrates fluid, such as the bodily fluids described with reference to FIG. 1. The fluid may transport the reagents across the absorbent substrate 102 and may include TSST-1 antigens, fluid particles (e.g., particles suspended or dissolved in the fluid), or both. Row 220 illustrates a fluid particle which may include or correspond to bacteria (e.g., Staph bacteria) or other toxins (e.g., non-TSS toxins) in the fluid 610. The fluid particle may not react with the reagents of the device 100, such as the first antibodies of the reaction zone 108.

Referring to FIG. 3, an example indication of a positive test result output by the device 100 for detecting toxic shock syndrome toxins is depicted. In FIG. 3, a first diagram 302 illustrates antibody reactions of a positive test result and a second diagram 304 illustrates color changes of zones of the positive test result. The diagrams 302 and 304 illustrate the fluid contact area 106, the reaction zone 108, the test zone 110, and the control zone 112.

Referring to the first diagram 302, during administration of a test for detecting toxic shock syndrome toxins, fluid (not represented) is captured or absorbed by the fluid contact area 106, an absorbent substrate, or a combination thereof. The fluid (described with reference to FIG. 3) contains TSST-1 antigens, which are illustrated in the fluid contact area 106. After the fluid is captured, the fluid is transported to the reaction zone 108, such as by capillary action. As the fluid contains the TSST-1 antigens, first antibodies of the reaction zone 108 react with the TSST-1 antigens. For example, the first antibodies, including an enzyme or particle, bind with the TSST-1 antigens to form antibody complexes. The fluid, the antibody complexes, and unreacted first antibodies are transported to the test zone 110. As the fluid contains the antibody complexes, the antibody complexes react (e.g., bind with) second antibodies in the test zone 110 to activate the enzyme or particle (e.g., to release first dye). The fluid and the unreacted first antibodies are transported to the control zone 112. As the fluid contains the unreacted first antibodies, the unreacted first antibodies react (e.g., bind with) third antibodies of the control zone 112 to activate the enzyme or particle (e.g., to release second dye).

Referring to the second diagram 304, as the enzymes (or particles) of the antibody complexes were activated to release the first dye, the test zone 110 changes color to indicate a potentially positive test result. A potentially positive test result indicates that the fluid may contain TSST-1 antigens and that the fluid may have transported the antibody complexes from the reaction zone 108 to the test zone 110. As enzymes (or particles) of the first antibodies were activated to release the second dye, the control zone 112 changes color to indicate a successful test. As the test zone 110 and the control zone 112 both change color, a positive test result is indicated. In some implementations, the color change of the test zone 110 may be a different color change from the color change of the control zone 112. In other implementations, the test zone 110, the control zone 112, or both, may generate a different indication. For example, the test zone 110, the control zone 112, or both, may generate a magnetic indication or a fluorescent indication. To illustrate, the test zone 110 may generate a magnetic indication or a fluorescent indication and the control zone 112 may generate a color change. Thus, a quantitative positive or negative test result may be produced and a qualitative successful test indication may be produced.

Referring to FIG. 4, a diagram 400 illustrates example stages of a positive test result of the device 100 for detecting toxic shock syndrome toxins. Diagram 400 illustrates the device 100, including the absorbent substrate 102, the fluid contact area 106, the reaction zone 108, the test zone 110, and the control zone 112, at various stages 402-408.

A first stage 402 illustrates fluid 410 being received at the fluid contact area 106 of the device. The fluid 410 includes TSST-1 antigens 411 and fluid particles (not represented). The fluid 410 may include or correspond to wound exudate, bodily fluids, or a combination thereof, as described in FIG. 1. The reaction zone 108 includes first antibodies 412, and each of the first antibodies may be coupled to an enzyme 414. The test zone 110 includes second antibodies 422 and a first dye substrate 424. The control zone 112 includes third antibodies 432 and a second dye substrate 434.

A second stage 404 illustrates the device 100 after the TSST-1 antigens 411 have been transported (e.g., by the fluid 410) to the reaction zone 108. The fluid 410 and the TSST-1 antigens 411 may be transported to the reaction zone 108 by the absorbent substrate 102. For clarity in illustration, the fluid 410 and fluid particles have been omitted from the second stage 404 (and subsequent stages 406-408). The TSST-1 antigens 411 may react (e.g., bind) with the first antibodies 412 to form antibody complexes 442. As the first antibodies 412 are not bound to the reaction zone 108 (or a substrate thereof), the first antibodies 412 (e.g., the antibody complexes 442) may be transported by (e.g., suspended in) the fluid 410 to the test zone 110. In some implementations, all of the TSST-1 antigens may not react with the first antibodies 412 and the unreacted first antibodies 412 may be transported along with the fluid 410 to the test zone 110.

A third stage 406 illustrates the device 100 after the TSST-1 antigens 411, and the antibody complexes 442 have been transported to the test zone 110. The second antibodies 422 may be bound to the test zone 110 or immobilized within the test zone 110. The second antibodies 422 may react (e.g., bind) with the antibody complexes 442 to form a sandwiched antibody complex 452. The reaction of the antibody complexes 442 and the second antibodies 422 may cause an indication 454, such as a color change. For example, the enzyme 414 may activate or release the first dye substrate 424 to cause the indication 454. Additionally, the unreacted first antibodies 412 may be transported by (e.g., suspended in) the fluid 410 to the test zone 110. The unreacted first antibodies 412 may not bind with the second antibodies 422. As the second antibodies 422 are bound to the test zone 110 (or a substrate thereof), the sandwiched antibody complex 452 be bound to the test zone 110 and may not be transported by (e.g., suspended in) the fluid 410. Accordingly, the sandwiched antibody complex 452 may not migrate along with the fluid 410 to the control zone 112. The unreacted first antibodies 412 may be transported along with the fluid 410 to the control zone 112.

A fourth stage 408 illustrates the device 100 after the TSST-1 antigens 411 and the unreacted first antibodies 412 have been transported to the control zone 112. Additionally, a portion of the antibody complexes 442 may be transported to the control zone 112. For example, all of the antibody complexes 442 may not bind with the second antibodies 422 and may be transported to the control zone 112 by the fluid 410. The third antibodies 432 of the control zone 112 may react (e.g., bind) with the unreacted first antibodies 412, the antibody complexes 442, or both, to form a control antibody complex 462. The reaction of the third antibodies 432 with the unreacted first antibodies 412, the antibody complexes 442, or both, may cause an indication 464, such as a color change. For example, the enzyme 414 may activate or release the second dye substrate 434 to generate the indication 464. In other implementations, the third antibodies 432 may not be bound to the control zone 112. Thus, the device may indicate a positive test result responsive to receiving the fluid 410.

Referring to FIG. 5, an example indication of a negative test result output by the device 100 for detecting toxic shock syndrome toxins is depicted. In FIG. 5, a first diagram 502 illustrates antibody reactions of a negative test result and a second diagram 504 illustrates color changes of zones of the negative test result. The diagrams 502 and 504 illustrate the fluid contact area 106, the reaction zone 108, the test zone 110, and the control zone 112.

Referring to the first diagram 502, during administration of a test for detecting toxic shock syndrome toxins, fluid (not represented) is captured or absorbed by the fluid contact area 106, an absorbent substrate, or a combination thereof. The fluid (described with reference to FIG. 5) includes fluid particles and does not include TSST-1 antigens. Accordingly, the fluid particles (e.g., bacteria, non-TSS toxins, etc.) are illustrated in the fluid contact area 106 and the fluid contact area 106 does not contain TSST-1 antigens. The fluid particles may include or correspond to the fluid particle represented in row 220 of FIG. 2. After the fluid is captured, the fluid migrates, such as by capillary action, to the reaction zone 108. As the fluid contains no TSST-1 antigens, no reactions (e.g., antigen/antibody bindings) occur in the reaction zone 108 and no antibody complexes are formed. For example, first antibodies of the reaction zone 108 do not react (e.g., bind with) the fluid or components thereof. The fluid and first antibodies, which include an enzyme or particle, are transported to the test zone 110. As the fluid contains no antibody complexes, no reactions occur in the test zone 110. For example, the first antibodies do not bind with second antibodies. The fluid and the first antibodies are transported to the control zone 112. As the fluid contains the first antibodies, the first antibodies react with (e.g., bind to) the third antibodies of the control zone 112 to activate the enzyme or particle (e.g., to release second dye).

Referring to the second diagram 504, as enzymes (or particles) of the first antibodies were activated to release the second dye associated with the control zone 112, the control zone 112 changes color to indicate a successful test. A successful test indicates that the fluid has transported the first antibodies from the reaction zone 108 to the control zone 112. Additionally, the change of color in the control zone 112 and the lack of indication (e.g., no color change) in the test zone 110 indicates a negative test result for TSST-1. In other implementations, the control zone 112 may generate a different indication. For example, the control zone 112 may generate a magnetic indication or a fluorescent indication.

Referring to FIG. 6, a diagram 600 illustrates example stages of a negative test result of the device 100 for detecting toxic shock syndrome toxins. Diagram 600 illustrates the device 100, including the absorbent substrate 102, the fluid contact area 106, the reaction zone 108, the test zone, and the control zone 112, at various stages 602-608.

A first stage 602 illustrates fluid 610 being received at the fluid contact area 106 of the device. The fluid 610 includes fluid particles 611 and does not include TSST-1 antigens. The fluid 610 may include or correspond to wound exudate, bodily fluids, or a combination thereof, as described in FIG. 1. The fluid particles 611 may include or correspond to bacteria (e.g., Staph bacteria) and other toxins (e.g., non-TSS toxins) in the fluid 610, as described with reference to FIG. 2. The reaction zone 108 includes the first antibodies 412, and each of the first antibodies may be coupled to the enzyme 414. The test zone 110 includes the second antibodies 422 and the first dye substrate 424. The control zone 112 includes the third antibodies 432 and the second dye substrate 434.

A second stage 604 illustrates the device 100 after the fluid particles 611 have been transported to the reaction zone 108. The fluid 610 and the fluid particles 611 may be transported to the reaction zone 108 by the absorbent substrate 102. For clarity in illustration, the fluid 610 has been omitted from the second stage 604 (and subsequent stages 606-608). The fluid particles 611 may not react (e.g., bind) with the first antibodies 412 to form antibody complexes. As the first antibodies 412 are not bound to the reaction zone 108 (or a substrate thereof), the first antibodies 412 may be transported along with the fluid 610 to the test zone 110.

A third stage 606 illustrates the device 100 after the fluid particles 611 and the first antibodies 412 have migrated to the test zone 110. The second antibodies 422 may not react (e.g., bind) with the first antibodies 412 (e.g., unreacted first antibodies 412). As the second antibodies 422 may not react with the first antibodies 412, no indication (e.g., a color change) may be generated in the test zone 110. As the second antibodies 422 are bound to the test zone 110 (or a substrate thereof), the second antibodies 422 may not migrate along with the fluid 610 to the control zone 112. The (unreacted) first antibodies 412 may be transported along with the fluid 610 to the control zone 112.

A fourth stage 608 illustrates the device 100 after the fluid particles 611 and the (unreacted) first antibodies 412 have been transported to the control zone 112. The third antibodies 432 may react (e.g., bind) with the first antibodies 412 to form a control antibody complex 462. The reaction of the third antibodies 432 with the first antibodies 412 may cause an indication 464, such as a color change. For example, the enzyme 414 may activate or release the second dye substrate 434 to generate the indication 464. In other implementations, the third antibodies 432 may not be bound to the control zone 112. Thus, the device 100 may indicate a negative test result responsive to receiving the fluid 610.

Figure 7:
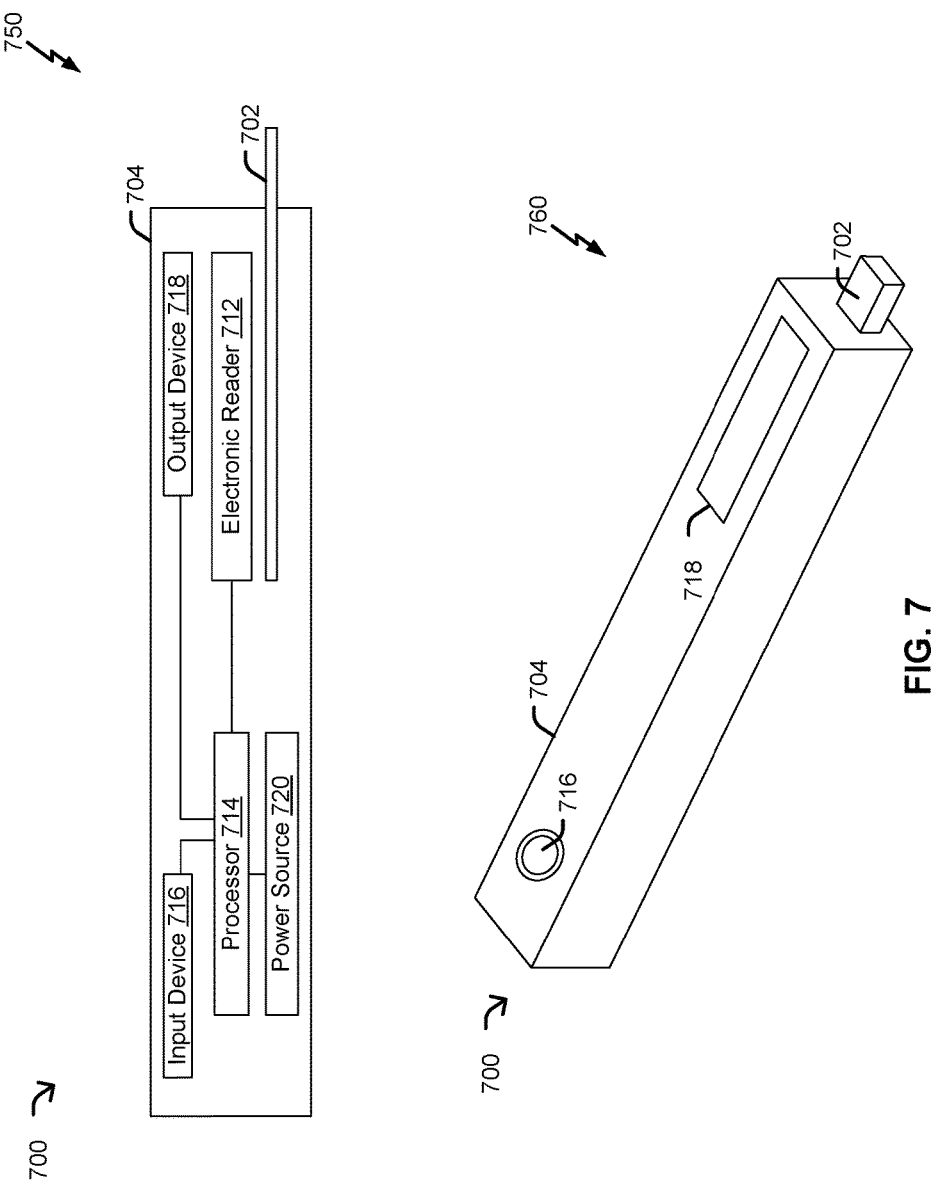
FIG. 7 is a diagram illustrating another implementation of a device for detecting toxic shock syndrome toxins.

Referring to FIG. 7, examples of a device 700 for detecting toxic shock syndrome toxins are depicted. FIG. 7 includes a first diagram 750 that includes a block diagram of the device 700 and includes a second diagram 760 that depicts an isometric view of the device 700. The device 700 may include or correspond to the device 100 of FIG. 1. The device 700 may include or correspond to an electronic testing device as an illustrative, non-limiting example. The device 700 may be configured to detect and indicate the presence of TSST-1, such as a quantitative amount of TSST-1 detected.

Referring to the first diagram 750, the device 700 includes an absorbent substrate 702, an electronic reader 712, a processor 714, an input device 716, an output device 718, and a power source 720. The absorbent substrate 702 may include or correspond to the absorbent substrate 102 of FIG. 1. The absorbent substrate 702 may include a pad and a membrane (e.g., a test area). The pad and the membrane may include or correspond to the pad 124 and the membrane 126, respectively, of FIG. 1. In some implementations, the absorbent substrate 702 may be removable from the device 700. By having a removable absorbent substrate, a second absorbent substrate may be inserted into the device 700 and, thus, the device 700 may be reusable.

One or more of the electronic reader 712, the processor 714, the input device 716, the output device 718, or the power source 720 may be included within a housing 704 of the device 700. The absorbent substrate 702 may be partially enclosed in the housing 704. For example, the pad, the membrane, or both, of the absorbent substrate 702 may be located within the housing 704. A sample pad (e.g., the fluid contact area 106 of FIG. 1) of the absorbent substrate 702 may be exposed (e.g., located outside of the housing 704).

The electronic reader 712 may be configured to read or analyze the membrane (e.g., the test zone 110, the control zone 112 if FIG. 1, or both) to enable the processor 714 to determine whether TSST-1 antigens are present in received fluid, such a fluid received via the absorbent substrate 702. In some implementations, the electronic reader 712 may be configured to generate data that enables the processor 714 to quantify an amount of TSST-1 antigens in the received fluid. To illustrate, the electronic reader 712 and the processor 714 may be configured to read, analyze, determine, or quantify, etc., an amount of fluorescent particles or magnetic particles in the membrane (e.g., the test zone, the control zone, or both).

In some implementations, the electronic reader 712 may include an image sensor, such as a complementary metal-oxide semiconductor (CMOS) or a charge-coupled-device (CCD), to detect fluorescent particles (e.g., one or more wavelengths associated with the fluorescent particles). The image sensor may be configured to generate data based on the membrane (e.g., the test zone, the control zone, or both) using particular wavelengths. The electronic reader 712 may generate image data and the processor 714 may be configured to execute image processing algorithms to process the image data (e.g., image intensities) to output a result or an indication. The device 700 may include or correspond to a fluorescent immunoassay (FIA).

In some implementations, the electronic reader 712 may include a magnetic field generator, a magnetic field sensor (e.g., a magnetometer), or both, to detect magnetic particles. The magnetic particles may include or correspond to magnetic beads (e.g., magnetic labels). As an illustrative, non-limiting implementation, the magnetic particles may include nano-sized iron oxide particles encapsulated or glued together with polymer. The electronic reader 712 may be configured to generate a magnetic field, read a magnetic field, or both, to generate magnetic field data. The electronic reader 712 may generate magnetic field data and the processor 714 may be configured to execute algorithms to process the magnetic field data to output a result or an indication. The device 700 may include or correspond to a magnetic immunoassay (MIA).

The processor 714 may be coupled to the electronic reader 712, the input device 716, the output device 718, and the power source 720. The processor 714 may be configured to execute one or more instructions stored in a memory (not shown). In some implementations, the memory may be accessible to the electronic reader 712, and the electronic reader 712 may execute one or more instructions.

The input device 716 may be coupled to the electronic reader 712 and may be configured to activate the electronic reader 712. For example, the input device may send a control signal to the processor 714. The input device 716 may include or correspond to a button or a switch.

The output device 718 may be coupled to the electronic reader 712, the input device 716, or both. The output device 718 may include or correspond to a light, a speaker, a display, or a combination thereof. As an illustrative, non-limiting example, the display may include a liquid crystal display (LCD). The output device 718 may be configured to output an indication in response to a signal from the processor 714. For example, the output device 718 may output a qualitative indication. To illustrate, the output device 718 may output a qualitative result that indicates that TSST-1 antigens are present or that an amount of TSST-1 antigens are greater than a threshold. Additionally or alternatively, the output device 718 may output a quantitative result that indicates an amount (e.g., a number or a concentration) of TSST-1 antigens.

The device 700 may also include the power source 720. The power source 720 may be coupled to the electronic reader 712, the processor 714, the input device 716, the output device 718, or a combination thereof. As an illustrative, non-limiting example, the power source 720 may include or correspond to a battery.

Referring to the second diagram 760, the isometric view of the device 700 is depicted. In the second diagram 760, the input device 716 is a button and the output device 718 is an LCD screen configured to display an output that indicates a positive test result, a negative test result, or an inconclusive test result. In a particular implementation, the input device 716 is activated (e.g., depressed by a user) thereby causing an activation signal to be sent from the processor 714 to the electronic reader 712. Responsive to the activation signal, electronic reader 712 obtains data from the absorbent substrate 702 and sends the data to the processor 714. The processor 714 analyzes the data and outputs indication data to the output device 718 based on the data. The output device 718 displays the indication data on the LCD screen. The indication data may indicate the positive test result, the negative test result, or the inconclusive test result for TSST-1 antigens.

Thus, FIG. 7 illustrates a device for detecting TSS toxins that include an electronic reader. By incorporating an electronic reader into a device for detecting TSS toxins, human error may be reduced and ease of use may be increased. By producing a quantitative output, a user or a medical professional may assess a severity of TSS. By including fluorescent particles or magnetic particles, an accuracy of the test may be increased as compared to colored particle based tests. Additionally, the device 700 may be used in-situ, as compared to conventional tests.

Referring to FIG. 8, an example of a method 800 of making a device for detecting toxic shock syndrome toxins. The device may include or correspond to the device 100 of FIG. 1, the device 700 (e.g., the absorbent substrate 702) of FIG. 7, or both. For example, the device may include or correspond to a testing strip, a testing device, a wound dressing, or a pad, among other articles. The device may provide an indication of the presence of TSS toxins.

The method 800 includes depositing a second antibody on a first zone of a membrane, where the second antibody is reactive with an antibody complex to cause a first indication, and where the antibody complex includes a first antibody coupled to a TSST-1 antigen, at 802. For example, the first zone may correspond to a test zone, such as the test zone 110 of FIG. 1. The first antibody (e.g., the first particular antibody as described with reference to FIG. 1) may include or correspond to one of the first antibodies (e.g., reaction zone antibodies) represented in row 204 of FIG. 2 or one of the first antibodies 412 of FIGS. 4 and 6. The second antibody may include or correspond to one of the second antibodies (e.g., the test zone antibodies) represented in row 208 of FIG. 2 or one of the second antibodies 422 of FIGS. 4 and 6. The TSST-1 antigens may include or correspond to the TSST-1 antigens as described with reference to at least the TSST-1 antigens of FIG. 1 and the antigens represented in row 202 of FIG. 2. In some implementations, the first antibody may be a monovalent antibody, a polyvalent antibody, a monospecific antibody, a monoclonal antibody, or a combination thereof. Depositing antibodies (e.g., the first antibodies, the second antibodies or the third antibodies) or a dye substrate (e.g., the first dye substrate or the second dye substrate) may include or correspond to treating, applying, spraying, dispersing, or forming the antibodies or the dye substrate on or within the membrane.

The method 800 includes depositing a third antibody on a second zone of the membrane, where the third antibody is reactive with a fourth antibody to cause a second indication, at 804. The second zone may correspond to a control zone, such as the control zone 112 of FIG. 1. For example, the third antibody may include or correspond to one of the third antibodies (e.g., control zone antibodies) represented in row 212 of FIG. 2 or one of the third antibodies 432 of FIGS. 4 and 6. The fourth antibody (e.g., the second particular antibody as described with reference to FIG. 1) may include or correspond to one of the first antibodies (e.g., reaction zone antibodies) represented in row 204 of FIG. 2 or one of the first antibodies 412 of FIGS. 4 and 6. In some implementations, the first antibody and the fourth antibody are the same type (e.g., both are first antibodies as described with reference to FIG. 1).

In some implementations, the method 800 may include coupling a pad to the membrane, the pad including the first antibody (e.g., the first particular antibody) and the fourth antibody (e.g., the second particular antibody). The pad may correspond to a reaction zone, such as the reaction zone 108 of FIG. 1. The third antibodies may be deposited on the second zone of the membrane before or after the pad is coupled to the membrane.

In some implementations, the method 800 may include forming a fluid contact area, such as the fluid contact area 106 of FIG. 1, configured to absorb a fluid. The fluid may include or correspond to the fluid 410 of FIG. 4 or the fluid 610 of FIG. 6. The fluid contact area may be positioned adjacent to the reaction zone. The reaction zone may be located between the fluid contact area and the test zone, and the test zone may be located between the reaction zone and the control zone.

In some implementations, the membrane may include a first dye substrate and a second dye substrate, and each of the first antibody (e.g., the first particular antibody) and the fourth antibody (e.g., the second particular antibody) may be coupled to an enzyme. For example, the first dye substrate may include or correspond to the first dye substrate 424 of FIGS. 4 and 6. The second dye substrate may include or correspond to the second dye substrate 434 of FIGS. 4 and 6. The enzyme may include or correspond to the enzyme 414 of FIGS. 4 and 6, a colored particle, a fluorescent particle, a magnetic particle, or a combination thereof.

In other implementations, a particle may be coupled to first antibodies instead of the enzyme. The particle may include colored latex, gold, a fluorescent material, or a magnetic material. In such implementations, the first zone (e.g., the test zone 110) may output a first indication and the second zone (e.g., the control zone 112) may output a second indication. For example, the antibody complexes binding with the second antibodies may cause the first indication in the first zone (e.g., the test zone 110), and the first antibodies (or antibody complexes) binding with the third antibodies may cause the second indication in the second zone (e.g., the control zone 112). The indication may include a color change, a fluorescent response, a magnetic response, an electrical response, a thermal response, a chemical response, or a combination thereof.

In some implementations, the method 800 may include forming an absorbent substrate configured to transport received fluid to the test area. The absorbent substrate, such as the absorbent substrate 102 of FIG. 1 or the absorbent substrate 702 of FIG. 7, may include the test area. In some implementations, the method 800 may further include inserting the absorbent substrate into at least one of a testing strip, a product, or other composite article. In a particular implementation, the testing device is configured to indicate a concentration of TSST-1 antigens in the first zone (e.g., the test zone 110), indicate that a threshold amount of TSST-1 antigens are present in the first zone, or a combination thereof.

In some implementations, the absorbent substrate is configured to transport the fluid via capillary action (e.g., wicking) from the sample pad (e.g., the fluid contact area 106) to the membrane. In some implementations, the absorbent substrate includes cellulose fibers, synthetic fibers, cellulose nanofibers, synthetic nanofibers, or a combination thereof. In some implementations, the absorbent substrate includes a hydrophilic material.

In a particular implementation, the second antibodies are immobilized, and the first dye substrate and the second dye substrate are the same dye substrate. The immobilized second antibodies may be further configured to not bind with the first antibodies. In a particular implementation, the third antibodies are immobilized within the second zone (e.g., the control zone).

In some implementations, the first antibodies and the (immobilized) second antibodies include a sandwich enzyme-linked immunoabsorbant assay (ELISA), and each of the antibody complexes includes a first antibody bound to a TSST-1 antigen.

Alternatively, a method of making a device for detecting toxic shock syndrome toxins includes coupling a pad to a membrane. The pad may include first antibodies which may include a first particular antibody and a second particular antibody. Each of the first particular antibody and the second particular antibody are associated with toxic shock syndrome toxin one (TSST-1). Each of the first antibodies are configured to react with a TSST-1 antigen to form an antibody complex. The membrane may include a second antibody configured to react with the antibody complex to cause a first indication and a third antibody configured to react with the second particular antibody to cause a second indication. In such implementations, the first particular antibody and the second particular antibody (e.g., the fourth antibody) may correspond to one of the first antibodies of FIG. 1, the second antibody may correspond to one of the second antibodies of FIG. 1, and the third antibody may correspond to one of the third antibodies of FIG. 1.

One or more operations of the method 800 may be performed by a person. Additionally or alternatively, one or more operations of the method 800 may be performed by a system (e.g., an automated system). For example, a system, such as a fabrication system, may include a processor and a memory. The system, such as the fabrication system, may further include specialized hardware or devices that perform operations of the method 800 in response to receiving commands from the processor.

The memory may include processor-executable instructions that, when executed by the processor, cause the processor to initiate or control formation of a device, such as the device 100 of FIG. 1, the device 700, or the absorbent substrate 702 of FIG. 7. In some implementations, the memory is a non-transitory computer-readable medium storing computer-executable instructions that are executable by the processor to cause the processor to initiate formation of a device in accordance with at least a portion of the method 800 of FIG. 8.

The system (e.g., the fabrication system) may be fully automated or partially automated (e.g., include one or more human performed operations). For example, a fabrication process performed by the system may be automated according to a schedule. The system may include fabrication equipment (e.g., processing tools) to perform one or more operations to form a device for detecting toxic shock syndrome toxins, such as the device 100 of FIG. 1, the device 700, or the absorbent substrate 702 of FIG. 7. For example, the fabrication equipment may be configured to form one or more pads, to form one or more membranes, to deposit one or more reagents (e.g., antibodies) on the one or more pads, the one or more membranes, or both, to couple the one or more pads to the one or more membranes, to divide (e.g., cut) the one or more pads (e.g., a bulk pad) into individual pads, to divide (e.g., cut) the one or more membranes (e.g., a bulk membrane) into individual membranes, to attach a backing to the device, to insert the device into a housing, to seal the device, etc., or a combination thereof, as illustrative, non-limiting examples.

The system (e.g., an automated system that performs the fabrication process) may have a distributed architecture (e.g., a hierarchy). For example, the system may include one or more processors, one or more memories, and/or one or more controllers that are distributed according to the distributed architecture. The distributed architecture may include a high-level processor that controls or initiates operations of one or more low-level systems. For example, a high-level portion of the fabrication process may include one or more processors, and the low-level systems may each include or may be controlled by one or more corresponding controllers. A particular controller of a particular low-level system may receive one or more instructions (e.g., commands) from a particular high-level system, may issue sub-commands to subordinate modules or process tools, and may communicate status data back to the particular high-level. Each of the one or more low-level systems may be associated with one or more corresponding pieces of fabrication equipment (e.g., processing tools). In some implementations, the system may include multiple processors that are distributed in the system. For example, a controller of a low-level system component may include a processor.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. An apparatus comprising:
a pad that includes first antibodies, the first antibodies comprising a first particular antibody and a second particular antibody, wherein each of the first antibodies are associated with toxic shock syndrome toxin one (TSST-1), the first particular antibody is configured to react with a TSST-1 antigen to form an antibody complex, the first particular antibody is coupled to a first particle, and the first particle comprises a magnetic material; and
a membrane coupled to the pad, the membrane including:
a first zone including an immobilized second antibody, wherein the immobilized second antibody is configured to react with the antibody complex to cause a first indication; and
a second zone including a third antibody, wherein the third antibody is configured to react with the second particular antibody to cause a second indication.

2. The apparatus of claim 1, wherein the second particular antibody is coupled to a second particle, wherein the first particle is configured to cause the first indication responsive to a reaction between the immobilized second antibody and the antibody complex, and wherein the second particle is configured to cause the second indication responsive to a reaction between the third antibody and the second particular antibody.

3. The apparatus of claim 2, wherein the first indication is a magnetic response.

4. The apparatus of claim 1, wherein the pad comprises a conjugate pad, and wherein the conjugate pad is configured to receive a fluid, to channel a first portion of the fluid and the first particular antibody to the first zone, and to channel a second portion of the fluid and the second particular antibody to the second zone.

5. The apparatus of claim 1, further comprising a sample pad coupled to the pad, the sample pad including a fluid contact area configured to receive fluid, wherein the fluid includes the TSST-1 antigen, wherein the first zone comprises a reaction zone, and wherein the second zone comprises a control zone.

6. The apparatus of claim 5, further comprising an absorbent substrate that includes the sample pad, the pad, and the membrane, wherein the absorbent substrate comprises a hydrophilic or a superhydrophilic material.

7. The apparatus of claim 6, wherein the absorbent substrate comprises cellulose fibers, synthetic fibers, cellulose nanofibers, synthetic nanofibers, or a combination thereof.

8. The apparatus of claim 1, further comprising a wound dressing, wherein the pad and the membrane are integrated into the wound dressing.

9. The apparatus of claim 1, further comprising a composite article, wherein the pad and the membrane are integrated into the composite article.

10. The apparatus of claim 1, wherein the pad and the membrane are integrated into a testing strip or a testing device.

11. The apparatus of claim 1, wherein the membrane comprises a lateral flow membrane, and wherein the membrane includes cellulose fibers, synthetic fibers, cellulose nanofibers, synthetic nanofibers, or a combination thereof.

12. The apparatus of claim 1, wherein the pad and the membrane are incorporated into a hygiene product or an applicator.

13. An apparatus comprising:

a pad that includes first antibodies, the first antibodies comprising a first particular antibody and a second particular antibody, where each of the first antibodies are associated with toxic shock syndrome toxin one (TSST-1), the first particular antibody is configured to react with a TSST-1 antigen to form an antibody complex, the first particular antibody is coupled to a first particle, the first particle comprises a magnetic material;

a membrane coupled to the pad, the membrane including:

a first zone including an immobilized second antibody, wherein the immobilized second antibody is configured to react with the antibody complex to cause a first indication; and a second zone including a third antibody, wherein the third antibody is configured to react with the second particular antibody to cause a second indication; and a sample pad coupled to the pad, the sample pad including a fluid contact area configured to receive fluid, wherein the fluid includes the TSST-1 antigen, wherein the first zone comprises a reaction zone, and wherein the second zone comprises a control zone, wherein the pad, the membrane, and the sample pad are integrated into a hygiene product or an applicator.

14. The apparatus of claim 13, wherein the second particular antibody is coupled to a second particle, wherein the first particle is configured to cause the first indication responsive to a reaction between the immobilized second antibody and the antibody complex, and wherein the second particle is configured to cause the second indication responsive to a reaction between the third antibody and the second particular antibody.

15. The apparatus of claim 13, further comprising an absorbent substrate that includes the sample pad, the pad, and the membrane, wherein the absorbent substrate comprises a hydrophilic or a superhydrophilic material.

16. The apparatus of claim 15, wherein the absorbent substrate comprises cellulose fibers, synthetic fibers, cellulose nanofibers, synthetic nanofibers, or a combination thereof.

17. An apparatus comprising:
   a pad that includes first antibodies, the first antibodies comprising a first particular antibody and a second particular antibody, wherein each of the first antibodies are associated with toxic shock syndrome toxin one (TSST-1), the first particular antibody is configured to react with a TSST-1 antigen to form an antibody complex; and
   a membrane coupled to the pad, the membrane including:
      a first zone including an immobilized second antibody, wherein the immobilized second antibody is configured to react with the antibody complex to cause a first indication; and
      a second zone including a third antibody, wherein the third antibody is configured to react with the second particular antibody to cause a second indication,
   wherein the first particular antibody is coupled to a first particle, the first particle comprising a magnetic material, wherein the second particular antibody is coupled to a second particle, wherein the first particle is configured to cause a magnetic response indicating a reaction between the immobilized second antibody and the antibody complex, and wherein the second particle is configured to cause the second indication responsive to a reaction between the third antibody and the second particular antibody.

* * * * *